(12) United States Patent
Szybisty et al.

(10) Patent No.: US 9,499,840 B2
(45) Date of Patent: Nov. 22, 2016

(54) POWERED STOWABLE VEHICLE SEAT AND ASSOCIATED SEAT FRAME ASSEMBLY

(71) Applicant: LEAR CORPORATION, Southfield, MI (US)

(72) Inventors: Robert Szybisty, Livonia, MI (US); Andrzej Dlugokecki, Troy, MI (US); Mark R. Keyser, Lake Orion, MI (US)

(73) Assignee: Lear Corporation, Southfield, MI (US)

( * ) Notice: Subject to any disclaimer, the term of this patent is extended or adjusted under 35 U.S.C. 154(b) by 0 days.

(21) Appl. No.: 14/707,256

(22) Filed: May 8, 2015

(65) Prior Publication Data

US 2015/0321586 A1 Nov. 12, 2015

Related U.S. Application Data

(60) Provisional application No. 61/991,885, filed on May 12, 2014.

(51) Int. Cl.
| | |
|---|---|
| *B60N 2/36* | (2006.01) |
| *C12P 7/08* | (2006.01) |
| *B60N 2/30* | (2006.01) |
| *B60N 2/02* | (2006.01) |
| *B60N 2/64* | (2006.01) |
| *C12P 7/06* | (2006.01) |
| *A61K 35/76* | (2015.01) |
| *A01N 63/02* | (2006.01) |
| *A61K 38/16* | (2006.01) |
| *C07K 14/335* | (2006.01) |
| *C12N 15/52* | (2006.01) |
| *A01N 37/44* | (2006.01) |
| *A01N 43/90* | (2006.01) |

(52) U.S. Cl.
CPC ............... *C12P 7/08* (2013.01); *A01N 37/44* (2013.01); *A01N 43/90* (2013.01); *A01N 63/02* (2013.01); *A61K 35/76* (2013.01); *A61K 38/164* (2013.01); *B60N 2/0232* (2013.01); *B60N 2/309* (2013.01); *B60N 2/3011* (2013.01); *B60N 2/3061* (2013.01); *B60N 2/64* (2013.01); *C07K 14/335* (2013.01); *C12N 15/52* (2013.01); *C12P 7/06* (2013.01)

(58) Field of Classification Search
CPC ...... B60N 2/309; B60N 2/64; B60N 2/3011; B60N 2/0232; B60N 2/3061
USPC ............... 297/331, 334, 378.12, 378.13
See application file for complete search history.

(56) References Cited

U.S. PATENT DOCUMENTS

| | | | |
|---|---|---|---|
| 4,637,653 A * | 1/1987 | Yoshida | ............... B60N 2/305 297/334 X |
| 6,012,755 A | 1/2000 | Hecht et al. | |
| 6,578,919 B2 | 6/2003 | Seibold et al. | |

(Continued)

*Primary Examiner* — Rodney B White
(74) *Attorney, Agent, or Firm* — Brooks Kushman P.C.

(57) ABSTRACT

A vehicle seat has a seat frame assembly including a seat base frame that may be shifted between a raised position and a lowered position, and a seatback frame pivotally attached to the seat base frame and foldable from a vertical position to a position atop the collapsed base frame. The seat base frame is pivotally connected to the vehicle floor by at least one front pivot leg which is pivotally connected for rotation with respect to both the vehicle floor and the base frame. A motor is mounted in a stationary position on the vehicle floor and connected to provide a relative torque between the seat base frame and one of the at least one pivot legs for powered movement of the seat base frame to and from the use position and the stow position.

16 Claims, 7 Drawing Sheets

(56) References Cited

U.S. PATENT DOCUMENTS

| | | |
|---|---|---|
| 6,966,598 B2 | 11/2005 | Schmale |
| 7,066,539 B2 * | 6/2006 | Hatta ................. B60N 2/01583 297/334 X |
| 7,252,337 B2 * | 8/2007 | Hofmann ................. B60N 2/20 297/331 |
| 7,255,399 B2 | 8/2007 | White et al. |
| 7,267,406 B2 | 9/2007 | Sturt |
| 7,328,929 B2 | 2/2008 | Epaud |
| 7,387,333 B2 | 6/2008 | Seibold |
| 7,497,517 B2 * | 3/2009 | Gundall ................. B60N 2/206 297/334 X |
| 7,600,801 B2 * | 10/2009 | Lehy ................. B60N 2/0232 297/331 X |
| 7,686,389 B2 * | 3/2010 | Yamada ................. B60N 2/3013 297/334 X |
| 7,878,592 B2 * | 2/2011 | Yamada ................. B60N 2/22 297/334 X |
| 7,891,737 B2 * | 2/2011 | Mather ................. B60N 2/3011 297/334 X |
| 8,444,223 B2 * | 5/2013 | Moegling ............. B60N 2/3013 297/331 X |
| 8,480,051 B2 * | 7/2013 | Muhlberger ......... B60N 2/3065 297/334 X |
| 8,585,147 B2 | 11/2013 | Calvert |
| 8,845,026 B2 * | 9/2014 | Kobayashi ........... B60N 2/3013 297/334 X |
| 8,911,017 B2 * | 12/2014 | Deptolla ............. B60N 2/3031 297/334 |
| 2006/0214477 A1 * | 9/2006 | Fukada ............. B60N 2/01583 297/334 X |
| 2012/0056460 A1 * | 3/2012 | Baker ...................... B60N 2/20 297/331 |
| 2015/0375643 A1 * | 12/2015 | Fisher .................... B60N 2/015 297/334 |

* cited by examiner

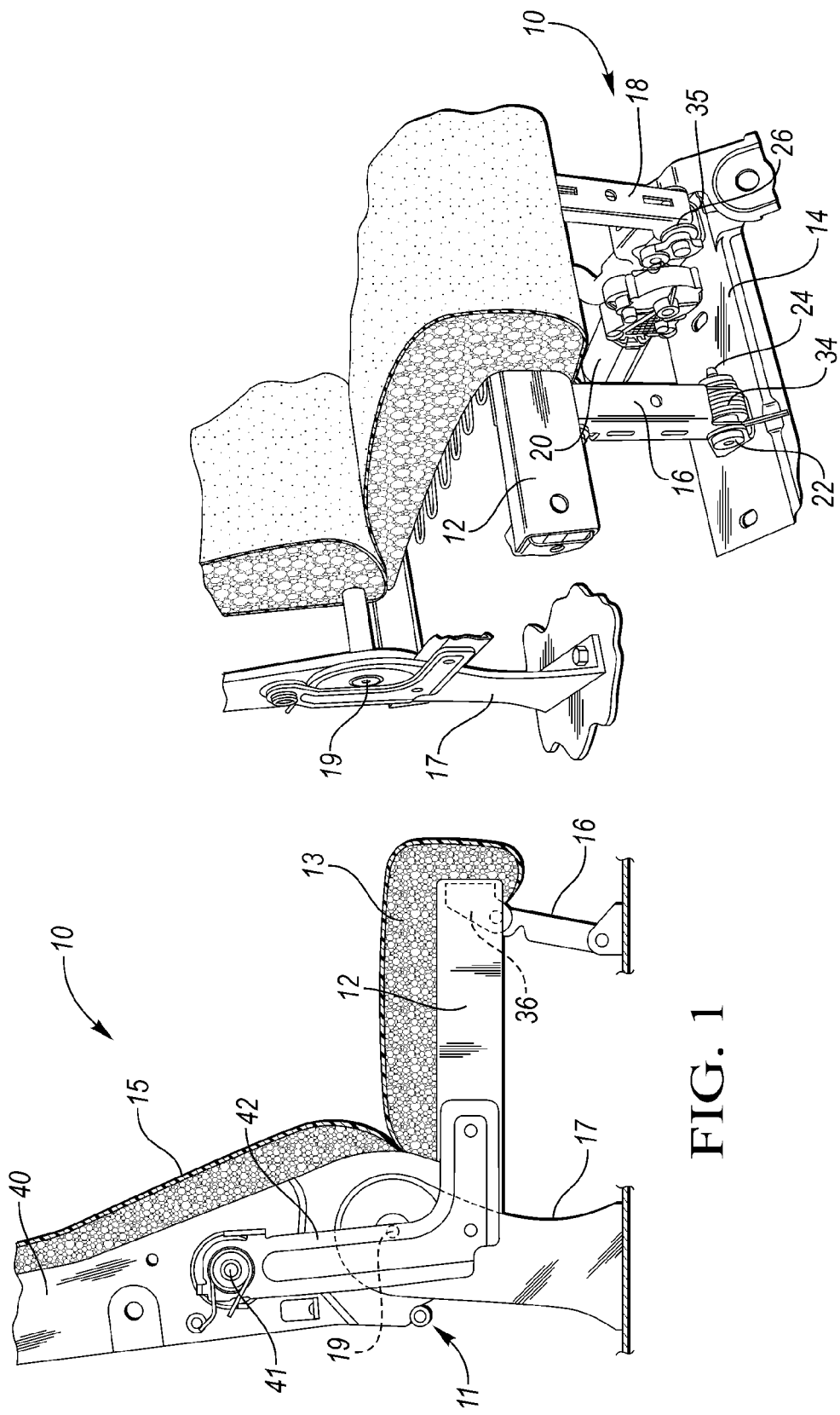

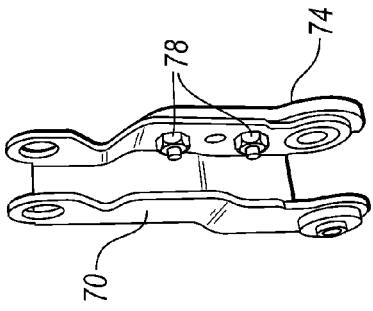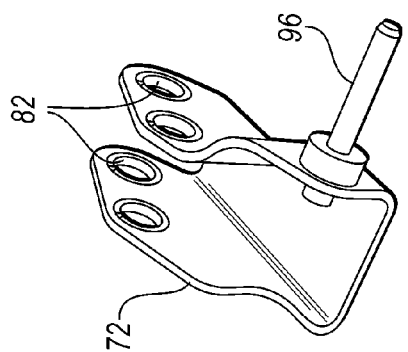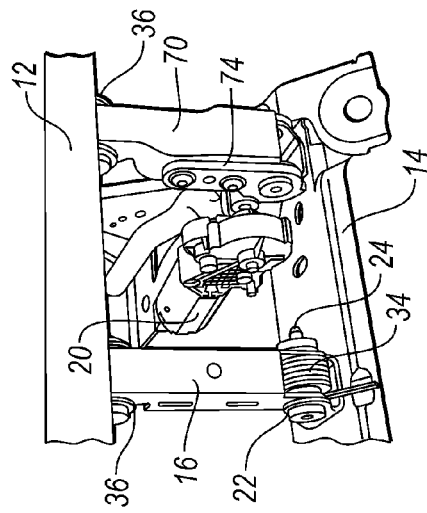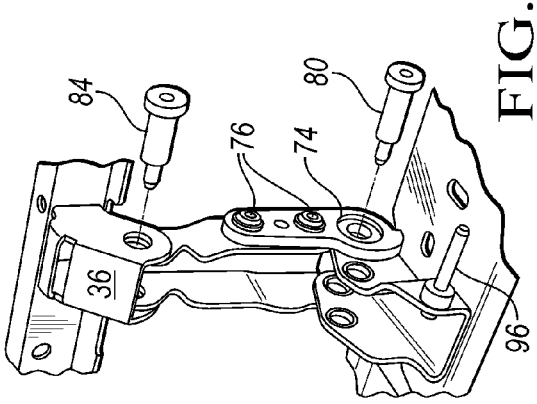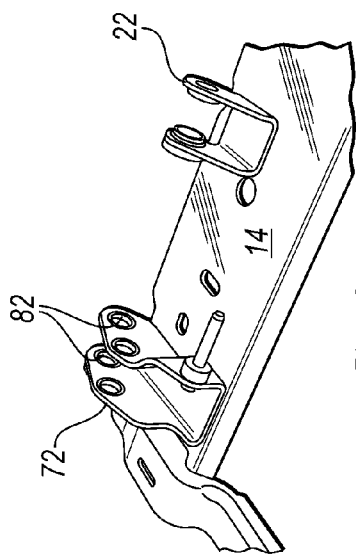

POWERED STOWABLE VEHICLE SEAT AND ASSOCIATED SEAT FRAME ASSEMBLY

CROSS-REFERENCE TO RELATED APPLICATIONS

This application claims the benefit of U.S. provisional application Ser. No. 61/991,885 filed May 12, 2014, the disclosure of which is hereby incorporated in its entirety by reference herein.

TECHNICAL FIELD

The present invention relates to vehicle seat powered stowing mechanisms.

BACKGROUND

Sport-utility vehicles, minivans, and crossover vehicle designs often include auxiliary or third-row seats which may be adjustable from a seating position for accommodating passengers, to a folded or stowed position to provide cargo space.

Current third-row vehicle seat designs often include a seat base having a base frame that shifts between a raised position and a lowered position, and a seatback attached to the seat base which may be folded forward, such that the vehicle seat may be quickly collapsed into a stowed position when additional cargo space is desired. U.S. Pat. Nos. 6,012,755 and 8,585,147 disclose two such stowable seat designs.

It is also known to integrate a motor into the seat-folding assembly to provide power to facilitate or assist in folding or stowing the seat and/or returning the seat to its passenger use position. However, there are several drawbacks to the existing powered folding seat designs.

First, the motors in existing designs are typically mounted on the seatback. Though this location may provide advantages in operably connecting the motor to the seatback and seat base, there may not be adequate space in some seatback frames to accommodate the motor and drive train necessary to provide a power assist to raise and stow the seat.

Second, the addition of a motor and its interconnecting parts to the seatback frame may provide additional limitations to seatback styling and comfort, since the size of the foam portion of the seatback may need to be reduced to provide space for the motor and the hard plastic shields utilized to cover the motor assembly within the seatback frame.

Third, additional shielding of the back portion of the seatback may be required to protect the motor assembly from damage from cargo when the seat is in the stowed position.

Fourth, depending on the particular seat design, placement of a drive motor in the seatback may add mass to the moving seatback. In these circumstances, it may then be necessary to re-design the seatback structure to compensate for this additional mass to provide adequate strength to withstand inertial forces in the event of an undesired vehicle impact.

Also, the motors utilized in existing powered folding seats are often both relatively large and loud (to provide the necessary torque to fold/raise the seat quickly), or relatively small and quieter, but slower in operation.

SUMMARY

According to one aspect of the present disclosure, a vehicle seat is disclosed for a vehicle that has a seat frame assembly including a seat base having a seat base frame that may be shifted between a raised position and a lowered position, and a seatback attached to the seat base by a hinge and foldable from a seating position in which the seatback is relatively vertical, to a folded-forward position in which the seatback is generally parallel and atop the collapsed base frame. The seat base frame is pivotally connected to the floor of the vehicle by virtue of a riser assembly that includes at least two front pivot legs, each of which are connected for pivotal rotation with respect to both the vehicle floor and the base frame. A motor is mounted in a stationary position (with respect to the vehicle floor) and operably connected to at least one of the pivot legs to drive the pivot legs from a generally vertical orientation whereby the seat base frame is in its raised seating position, to a generally horizontal orientation whereby the seat base frame is in its lowered, stowed position.

According to another aspect of the disclosure, a vehicle seat and associated seat frame assembly of the type described above may also include a drive linkage interconnecting the motor and/or riser assembly with the seatback hinge to provide power to raise and/or lower the seatback as the seat base frame is raised or lowered.

According to another aspect of the disclosure, a force-assisting device, such as a spring, may be provided at the seatback hinge drive link to assist in urging the seatback from its generally vertical seating position to its folded-forward position.

According to another aspect of the disclosure, additional springs may be utilized to bias the riser assembly towards its upright position and assist the motor in moving the seat base frame and seatback from their stowed to their seating positions.

These and other aspects of the disclosure will be more fully explained with reference to the attached drawings and the following detailed description.

BRIEF DESCRIPTION OF THE DRAWINGS

FIG. 1 is a side partial cut-away view of an embodiment of the powered stowable vehicle seat including an embodiment of the seat frame assembly;

FIG. 2 is a fragmentary front left perspective partial cut-away view of a first embodiment of a powered stowable seat with the base frame in the raised position;

FIG. 8 is a fragmentary front perspective view of a second embodiment of a powered stowable seat frame with the base frame in the raised position;

FIG. 9 is a fragmentary rear perspective view of the vehicle seat riser with pivot base brackets;

FIG. 10 is a rear perspective view of a pivot base bracket and motor anti-rotation pin;

FIG. 11 is a front perspective view of a front base frame pivot leg;

FIG. 12 is a rear perspective view of a portion of the seat frame riser assembly including a front pivot leg, base bracket, and seat base frame bracket;

DETAILED DESCRIPTION

Figure 3:
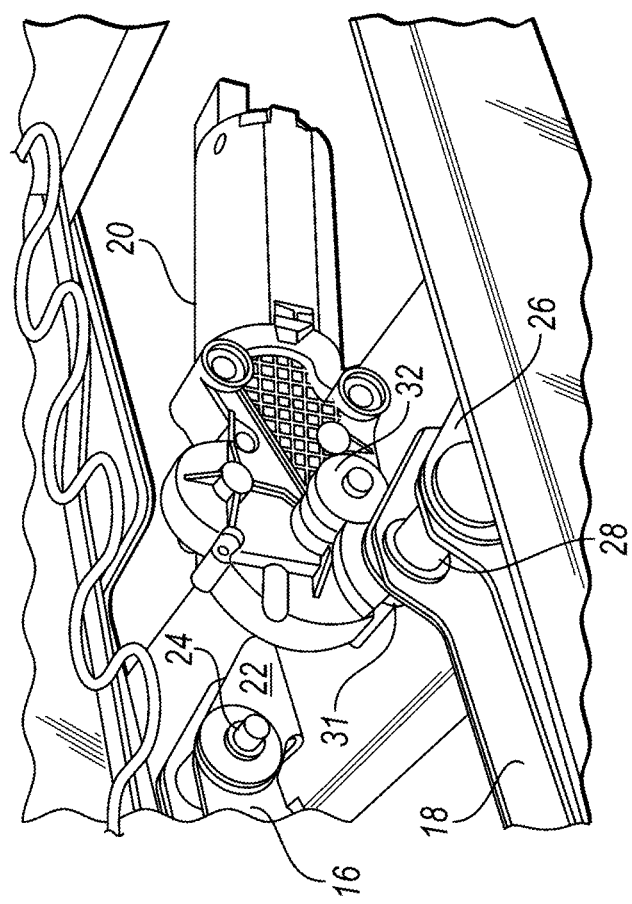
FIG. 3 is a fragmentary front right perspective view of the powered stowable seat of FIG. 2 with the seat base frame in the lowered position.

As required, detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

Referring to FIGS. 1 and 2, a vehicle seat, generally indicated by reference numeral 10, is illustrated as it may be installed in a vehicle. The seat 10 includes a seat frame assembly, generally indicated by reference numeral 11, and suitable padding 13 (typically one or more foam pads), soft trim covering 15 (typically cloth, vinyl, and/or leather), and hard trim covering 54 (typically plastic, and shown in FIG. 7) covering at least a portion of the seat frame assembly to complete the seat 10.

The frame assembly 11 includes a seat base frame 12, which may be pivotally secured to a riser assembly 14, which in turn is secured to the floor of the vehicle. The frame assembly includes at least one pivot leg mounted on the forward portion of the frame 12. In this illustrated embodiment, the riser assembly includes two pivot legs 16 and 18. Each one of the pivot legs 16 and 18 are pivotally secured at their upper ends to a front portion of the seat base frame 12, and are pivotally secured at their lower ends to a front portion of the riser 14.

The seat frame assembly 11 may also include a seatback frame 40, which may be pivotally attached to the vehicle floor. In the disclosed embodiments, a pair of rear seatback attachment brackets (17 and not shown) are each secured at their lower ends to the vehicle floor, and are each pivotally secured at their upper ends to the lower portion of the seatback frame 40 at each side of the frame, such that the seatback may be moved from one or more seating positions to a stowed position folded over and generally parallel to the seat base.

The seat base frame 12 may be attached at its rear portion to a connecting bracket 42, which bracket 42 is also pivotally connected to the seatback frame 40 at pivoting axis 41.

The seat base frame 12 is thereby positionable between a seating position, wherein the pivot legs 16 and 18 are generally vertical and perpendicular to the seat base frame 12 and the vehicle floor, and a stowed, generally flattened position, wherein the pivot legs are generally horizontal and nearly parallel to the seat base frame 12 and the vehicle floor.

The upper ends of each of the pivot legs 16, 18 may be pivotally secured to pivot brackets 36 using pivot pins (not shown) in a conventional manner. The upper ends of each seatback bracket 17 may similarly be secured using conventional pins. The elements described thus far in this paragraph are well-known components of a vehicle seat which may be manually positioned between a seating position and a stowed or folded position.

Figure 7:
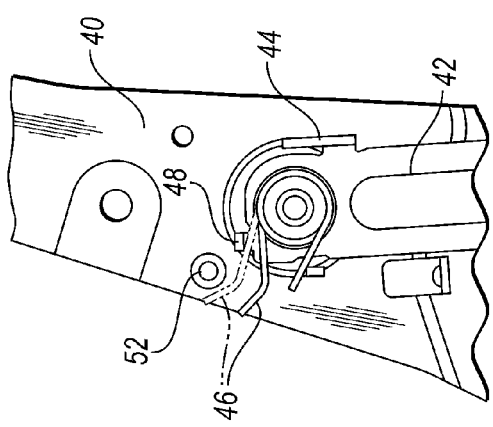
FIG. 7 is a fragmentary side view of the seatback frame and support bracket.

Referring to FIGS. 2, 3 and 7, the disclosed embodiments also include an electric drive motor 20 which may mounted in a relatively forward position beneath the seat in proximity to one of the pivot legs 16, 18, and operatively connected to the pivot leg to rotate the powered leg from the seating to the stowed position and vice versa. In the disclosed embodiments, the motor 20 may be secured, either directly or indirectly, to the riser 14 or the vehicle floor, such that the motor does not move as it is operated to apply a relative torque between the seat base 12 and the pivot legs 16, 18 to drive the seat base frame 12 and the seatback frame 14 from their in-use positions to their stowed positions. In each of the illustrated embodiments, the motor is mounted beneath the seat base frame 12 adjacent the left front pivot leg 18, 70. In the disclosed embodiments the motor is mounted in a manner in which the motor is not required to move with one of the moving seat components (e.g., the seatback or the seat base) as the seat is positioned between its seating and stowed positions.

It will be appreciated by those skilled in the art, however, that, consistent with the spirit of the invention, it is contemplated that the motor could be mounted in any manner in which the motor may be operatively connected to drive one of the pivot legs 16, 18 in any location where the motor and drive components may be drivingly connected to apply a relative torque between the seat base frame 12 and one of the pivot legs, yet are shielded by the seat frame from passengers' feet and cargo.

Referring still to FIGS. 2 and 3, any non-motor-driven pivot leg (such as front pivot leg 16) may be pivotally connected to the seat riser 14 using a conventional base bracket 22 and pivot pin 24. The motor-driven pivot leg 18 is also pivotally connected to the riser 14. However, the base bracket for the motor-driven pivot leg 18 may be of a slightly modified design to accommodate the drive components which interconnect the drive motor to the driven pivot leg 18. In the embodiment illustrated in FIGS. 2 and 3, pivot leg 18 is pivotally mounted to base bracket 26 via a drive pin 28 which includes an appropriately toothed drive gear 31 which engages and is rotationally driven by a conventional pinion gear 32 on the motor 20.

The motor 20 is operably connected to drive pivot leg 18, and rotate pivot leg 18 about its lower pivot axis 28. As the driven pivot leg 18 is rotated by the motor drive, front pivot leg 16 is similarly rotated about its lower pivot axis 24, and each of the pair of rear pivot legs are similarly rotated about their lower pivot pins to thereby move the seat base frame 12 from its seating position (shown in FIG. 2) to its stowed position (shown in FIG. 3) and vice versa.

Referring to FIGS. 2 and 7, the seat frame assembly 11 may also include one or more force-assist elements 34, such a spring(s), mounted at a pivot point on one or both of pivot legs 16, 18 (such as, for example, at 22 as shown) to provide a biasing force which urges the pivot legs to rotate upwardly towards their in-use position. In particular, in one contemplated embodiment, a second seat base spring (not shown) is also mounted at front pivot leg 18, 70, at location 35.

It will be appreciated by those skilled in the art that the biasing force provided by the spring element(s) 34 should be sufficient to assist the motor in counteracting the gravitational force moving the seat from its fully stowed position towards its seating position, but not so great a force that it provides a significant counterproductive resistance when the motor rotates the seat forward to its stowed position. It will also be appreciated by those skilled in the art that other conventional force-assist elements, such as, for example, torsion springs and/or hydraulic cylinders, may be employed to assist the motor over a portion or the entirely of the range of motion of the seat base as it is moved from its seating position (shown in FIG. 2) to its stowed position (shown in FIG. 3) and/or vice versa.

Referring now to FIGS. 4-7, the seat 10 may include a seatback 40 which is pivotally connected at pivot 41 to a seatback/seat base interconnecting bracket 42 for movement to and from a generally vertical seating position to a generally horizontal folded position. The seatback 40 may include a conventional drive linkage (not shown) which interconnects the seatback 40 with the seat base frame 12, such that, prior to initiation of movement of the seat base frame from its raised seating position to its collapsed stowed position, the seatback frame 40 is unlocked from its use position to simultaneously effect movement of the seatback from its generally vertical seating position to its stowed position, folded forward a top the collapsed seat base 12. A drive link bracket 44 may be provided to operatively connect the drive linkage to the power drive motor 20, or to another drive motor which may be controlled via a conventional electronic control unit to appropriately operate the drive linkage to unlock the seatback when powered movement of the seat from the use to the stowed position is desired.

Still referring to FIGS. 4-7, the seat 10 and seat frame 11 may also include at least power-assist element 46 to assist the power drive by urging the seatback forward at the initial stages of movement of the seatback from its locked seating position to its folded position, and/or vice versa. In the disclosed embodiment, one lost motion seatback return spring may be mounted at the seatback pivot 41 to provide a biasing force over a limited range of the seatback's pivotal motion by urging the seatback forward at the initial stages of movement of the seatback from its locked seating position to its folded position.

Figure 4:
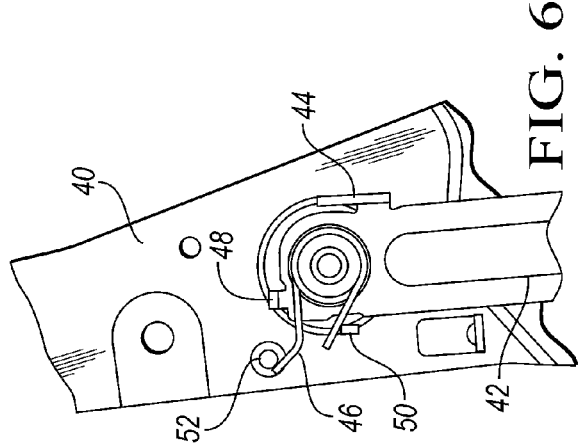
FIG. 4 is a fragmentary side view of the seatback frame and support bracket with the seatback in the folded position.
Figure 6:
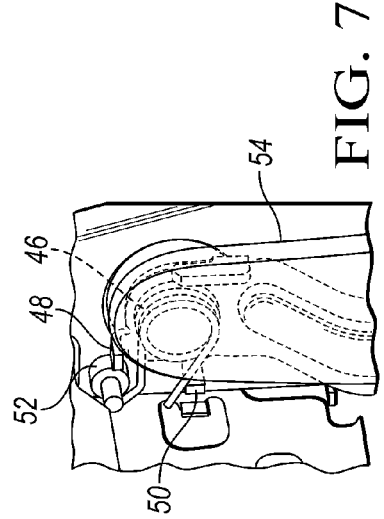
FIG. 6 is a fragmentary side view of the seatback frame and support bracket with the seatback in a fully raised position.
Figure 5:
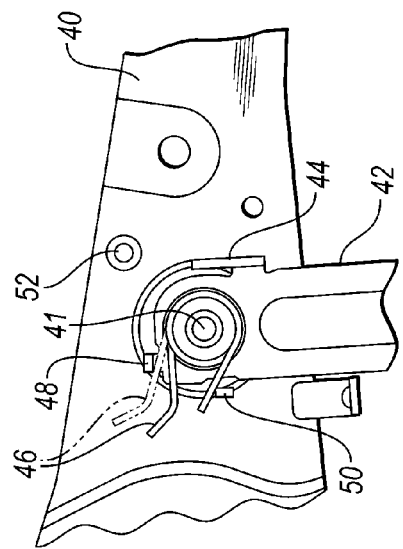
FIG. 5 is a fragmentary side view of the seatback frame and support bracket with the seatback in a partially raised position.

As shown in FIG. 4, when the seatback 40 is folded in the stowed position (at approximately 3° from horizontal), the return spring 46 does not provide any biasing force on the seatback 40. Instead, the spring ends are restrained from further expansion by tabs 48 and 50. As seatback 40 is raised towards its fully deployed seating position (such as, for example, at approximately 81° from horizontal, as shown in FIG. 5), one end of the return spring 46 is contacted by a pin 52 on the seatback 40. As the seatback moves from this intermediate position to its fully deployed seating position (as shown in FIG. 6) the return spring 46 is pre-loaded as the spring is compressed between pin 52 and tab 50. Thus, when the seatback is locked in its seating position (such as, for example, approximately 109° from horizontal) the return spring 56 is wound and will provides a biasing force on the pin 52 and, thereby, the seatback 40 when it is unlocked for forward movement.

In the disclosed embodiment, the use of one or more lost motion springs thus provides additional motive force, assisting the motor 20 for a limited range of movement of the seatback (such as, for example, from about 109° to 81° from horizontal) whenever the seatback is moved forward and downward from its seating position to its folded position, but the spring 56 does not increase the midrange lifting torque at the seatback is raised from its nearly horizontal folded position to the point (such as, for example, about 81° from horizontal) at which the spring 46 is preloaded.

It will thus be appreciated that the use of one or more force-assist elements in the disclosed power-driven stowable seat, such as lost motion seatback return springs, as well as one or more seat base assist springs, may lower the torque required of the motor to move the seat through its range of motion, thereby allowing the drive motor 20 to operate faster, quieter, and more efficiently, and requiring less power from the vehicle. It will also be appreciated that other lost motion force assist elements, such as a clock spring with a back-winder, may be utilized to provide a desired level of power assist, in one or both directions, to the moving seat frame components.

It will also be appreciated that, as shown in FIG. 6, the disclosed drive link bracket 44, return spring 46, and pin 52 provide minimal design/component differences between the disclosed powered stowable seat and a manual stowable seat, thereby minimizing part differences and part complexity, and maximizing commonality between the powered and manual designs. In particular, for example, as shown in FIG. 7, plastic shields, such as shield 54, and other aesthetic seat packaging components, may be employed interchangeably on both the manual and powered versions of a stowable seat.

FIGS. 8-14 illustrate another embodiment which employs an alternative motor drive assembly including pivot leg 70, pivot base bracket 72, and toothed sector plate 74. Sector plate 74 may be bolted on the drive side of pivot leg 70, and pivot leg 70 and sector plate 74 may be pivotally attached to the base bracket 72 using a conventional shoulder bolt 80, which is inserted through a first set of openings 82 in the base bracket 72. The upper end of pivot leg 70 may be pivotally attached to seat base frame 12 via bracket 36, also using a conventional shoulder bolt 84.

Figure 14:
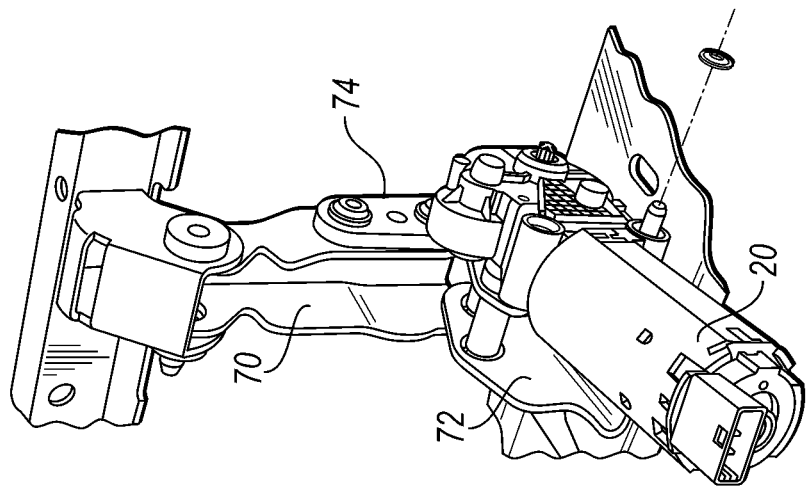
FIG. 14 is a fragmentary rear perspective view of the seat frame riser assembly with the motor installed thereon.
Figure 13:
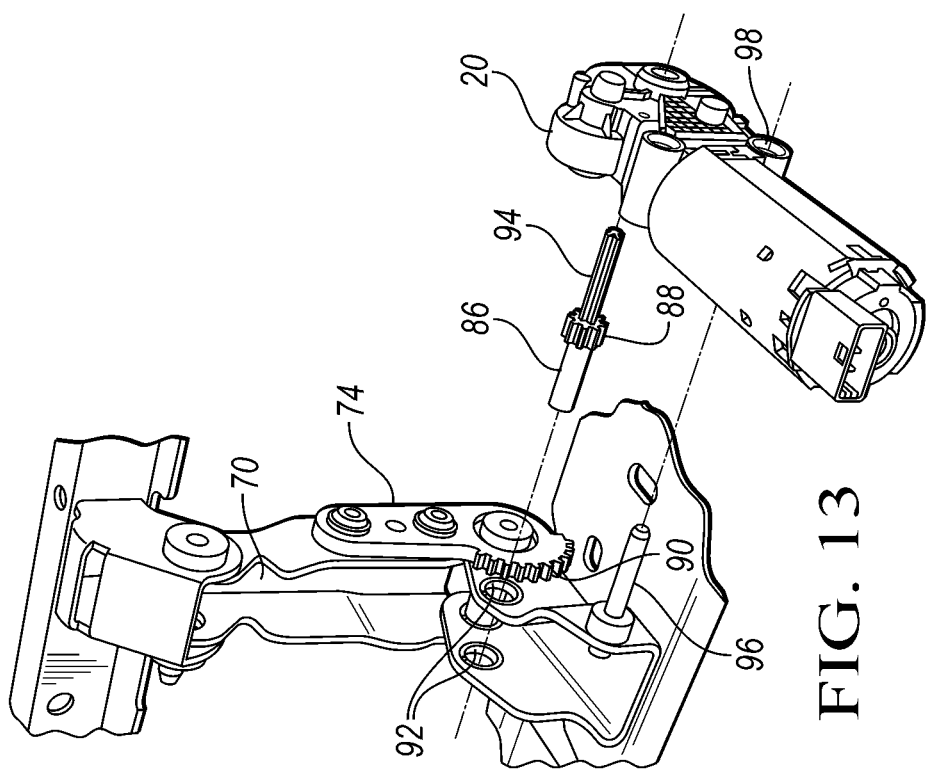
FIG. 13 is a fragmentary rear perspective exploded view of the portion of the seat frame riser assembly shown in FIG. 8, the motor/pinion shaft, and drive motor.

Referring in particular to FIGS. 13 and 14, drive pinion 86 operably interconnects motor 20 through engagement of tooth gears 88 with the toothed portion 90 of the sector plate 74, when the outboard shaft portion of the drive pinion 86 is installed in a second set of openings 92 in the base bracket 72, and the inboard shaft portion 94 of the drive pinion 86 is installed in the motor 20. An anti-rotation pin 96 may also be secured to the pivot base bracket 72, inserted in an opening 98 in the motor 20, and secured in place by conventional means, such as with a push-nut, to secure the motor 20 in place.

Each of the disclosed embodiments may also employ one or more conventional seatback adjustment (i.e., recliner) mechanisms which separately provide the capability of adjusting the inclination of the seatback to various desired use positions. It is contemplated that the disclosed powered seat stowage and return system control would be integrated with the associated inclination adjustment mechanisms so that inclination adjustment mechanisms are first unlocked upon activation and operation of the powered stow/return drive and, if desired, thereafter locked upon completion of the powered stowage/return operation.

It may also be desirable to provide a motor/drive-train combination and that is back-drivable, so that, for example, an external force on the seat does not damage the drivetrain. As will be appreciated by those skilled in the art, this can be achieved using the disclosed drivetrain embodiments by adopting an appropriate gear ratio and motor combination in a known manner.

It will be appreciated that the power drive assembly embodiment illustrated in FIGS. 8-14 provide a limited number of components uniquely associated with the powered stowable seat, such that assembly of both manual and powered versions of the seat may be manufactured with minimal tooling costs and manufacturing changes.

Figure 15:
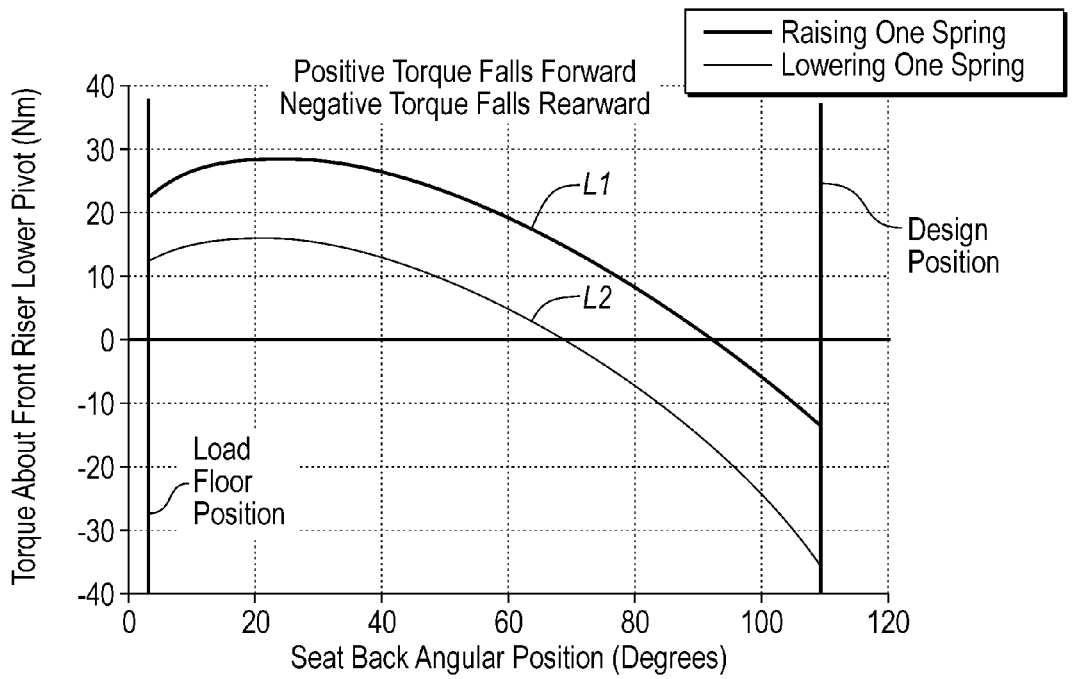
FIG. 15 is a graphical depiction of the expected range of torques required to raise and lower the seat (seatback and base frames) with spring force assistance from one seat base spring.

FIG. 15 illustrates the expected torque range required for a powered stowable seat having one seat base assist spring 34. In this chart, the expected torque (y-axis) required to raise the seat over the range of seatback angular positions (x-axis) is indicated by line L1, and the expected torque (y-axis) required to lower (stow) the seat over the range of seatback angular positions (x-axis) is indicated by line L2. The graphical depiction of this engineering simulation indicates that, with one seat base assist spring, the maximum torque required to raise the seat is just under 30 Newton-meters, and the maximum torque required to lower the seat is approximately −35 Newton-meters. While these expected torque requirements are an improvement over a system which does not include any spring assistance, additional spring assistance may be required to lower the torque requirements of a motor utilized in the disclosed embodiments.

Figure 16:
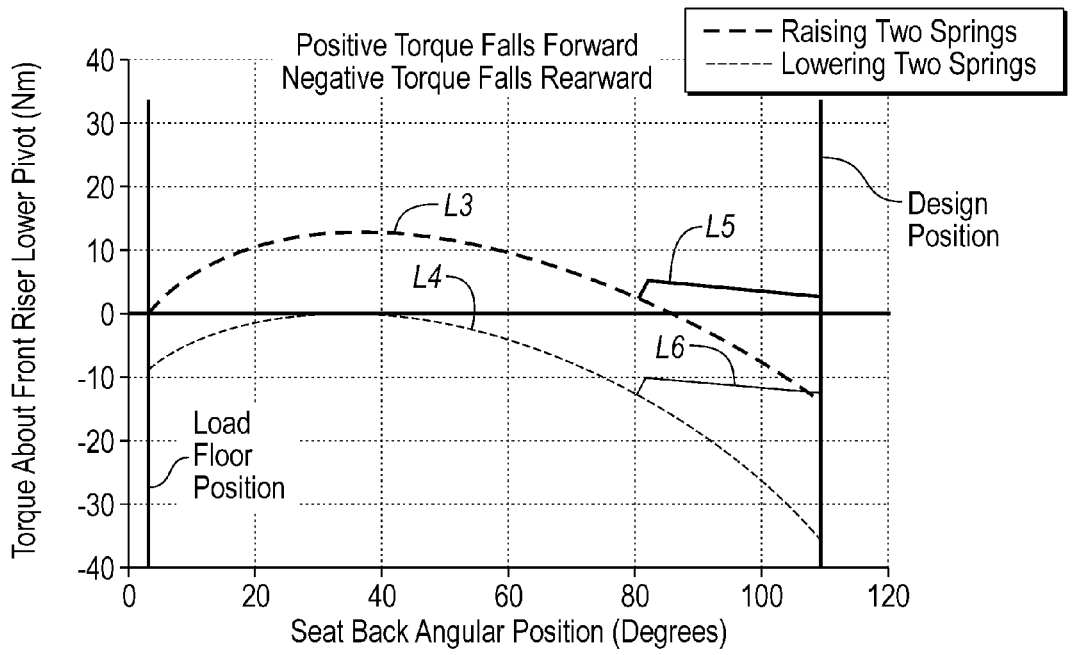
FIG. 16 is a graphical depiction of the expected range of torques required to raise and lower the seat (seatback and base frames) with spring force assistance from two seat base springs and one lost motion seatback return spring.

FIG. 16 illustrates the expected torque range required for a powered stowable seat having two base assist springs 34. In this chart, the expected torque (y-axis) required to raise the seat over the range of seatback angular positions (x-axis) is indicated by line L3, and the expected torque (y-axis) required to lower (stow) the seat over the range of seatback angular positions (x-axis) is indicated by line L4. The graphical depiction of this engineering simulation indicates that, with two seat base assist spring, the maximum torque required to raise the seat is reduced to less than 15 Newton-meters, and the maximum torque required to lower the seat remains at approximately −35 Newton-meters. Additional lines L5 and L6 depict the expected torque requirements in the range of movement of the seatback from 80-109° when a lost motion seatback assist spring is mounted on the seatback as previously described herein. Thus, it is expected that substantially less maximum torque (about −10 to −15 Nm) will be required to lower the seat with this arrangement.

It will therefore be appreciated that, by employing one or more seat base assist springs to assist in raising the seat base, and at least one lost motion assist spring to assist the moving seatback forward as the seat is powered to its stowed position, a lower torque motor can be utilized, thereby allowing for faster and quieter operation of the seat.

Figure 17:
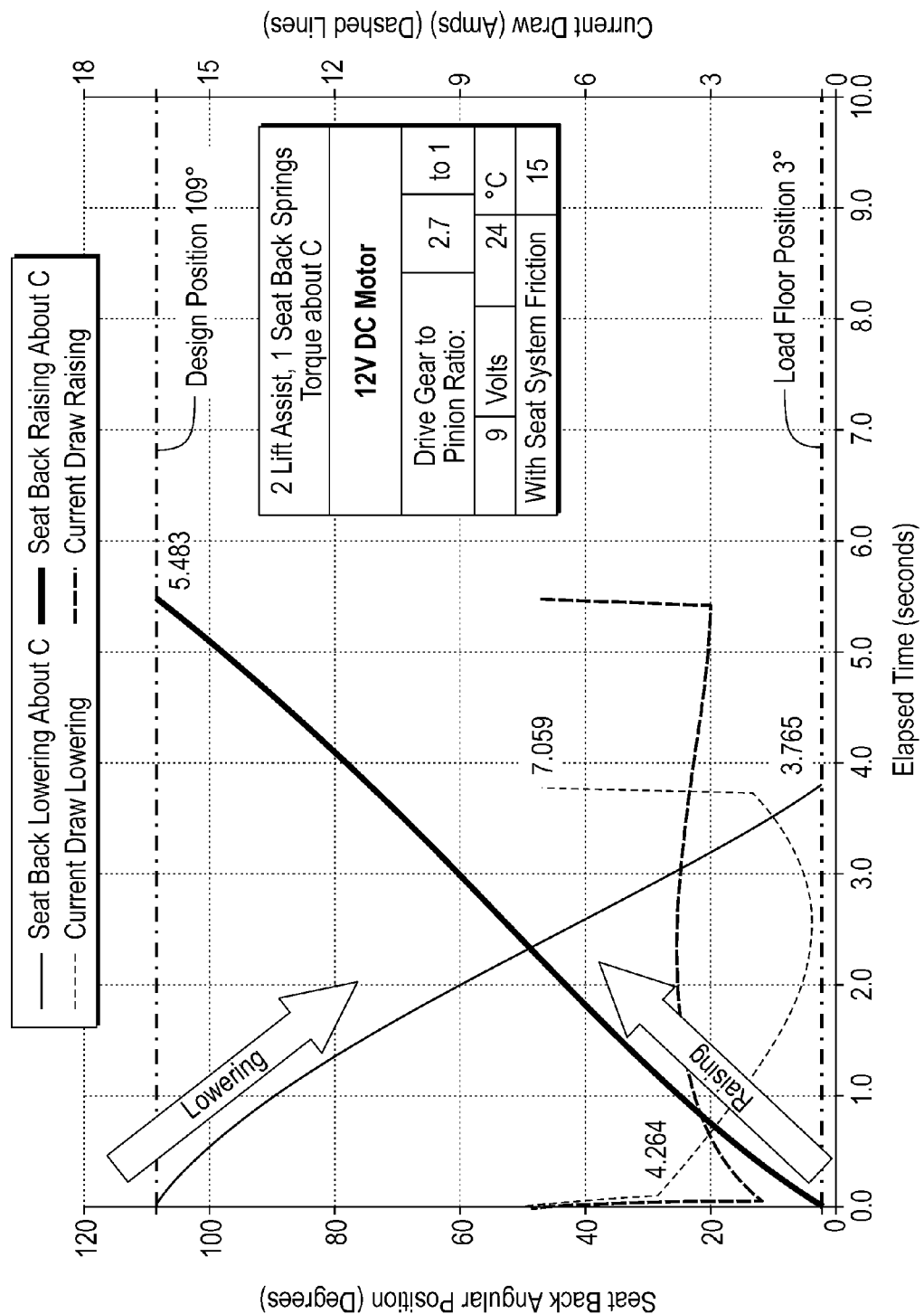
FIG. 17 is a graphical depiction of the expected elapsed time and current draw required to raise and lower the seat (seatback and base frames) with spring force assistance from two seat base springs and one lost motion seatback return spring.

FIG. 17 illustrates the expected approximate raising and lowering times for a powered stowable seat utilizing the present invention including a conventional 12 V DC motor (such as is available, for example, from Nidec Corporation). In the illustrated scenario, the motor is assumed to be driven at 9 V, and the seat includes two seat base assist springs and one lost motion seatback assist spring. As illustrated, a relatively rapid operation time (approximately 5.5 seconds to raise the seat, and approximately 3.75 seconds to stow the seat) is achieved with this arrangement. In another possible scenario, a motor driven at 11 volts with similar power-assist elements, raised the seat in approximately 4 seconds and a stowed the seat in approximately 3 seconds. It will be appreciated that other, similar benefits may be achieved with other motor operating voltages and speeds by utilizing the disclosed seat design with various combinations of power-assist elements.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. A seat frame assembly for a vehicle, the vehicle having a floor, the seat assembly comprising:
a seat base frame pivotally connected to the vehicle floor by a riser assembly, the riser assembly including at least two pivot legs, each of the pivot legs are connected at their lower end for pivotal rotation with respect to the vehicle floor, and at their upper end for pivotal rotation with respect to the seat base frame at a forward portion of the seat base frame for movement between a raised use position and a lowered stow position;
a seatback frame pivotally attached to the seat base frame for movement to and from a raised, generally vertical use position to a lowered, generally horizontal stow position, wherein the riser assembly further includes
at least two seatback/seat base interconnecting brackets, each of the seatback/seat base interconnecting brackets are connected at their forward ends to the seat base frame, and pivotally connected at their upper ends to the seatback frame for rotation of the seatback frame about a first pivoting axis, and
at least two seatback attachment brackets, each of the seatback attachment brackets are connected at their lower ends to the vehicle floor, and pivotally connected at their upper ends to the seatback frame for rotation of the seatback frame about a second pivoting axis that is lower than the first pivoting axis from a generally vertical orientation to a generally horizontal orientation with respect to the vehicle floor, such that pivotal rotation of the lower ends of the pivot legs with respect to the vehicle floor results in a corresponding forward and downward movement of the seatback frame and the seat base frame from their use positions to their stow positions; and
an electric drive motor operatively connected to provide a relative torque between the seat base frame and one of the pivot legs for powered movement of the seat base frame to and from the use position and the stow position.

2. The seat frame assembly of claim 1 wherein the drive motor is mounted in a stationary position with respect to the vehicle floor.

3. The seat frame assembly of claim 1 further including a drive linkage operably connecting the drive motor with the seatback frame to thereby provide power to unlock the seatback frame prior to powered movement of the seat from the use to the stow position.

4. The seat frame assembly of claim 1 further including at least one seat base force-assist element operably connected to at least one of the front pivot legs to provide a biasing force which urges the pivot legs to rotate the seat base toward the use position.

5. The seat frame assembly of claim 1 wherein the seatback frame is attached to the seat base frame by two pivots located on opposite sides of the seatback frame, and further including a force-assist element operably connected at one of the pivots to provide a biasing force to urge the seatback frame from its generally vertical use position to its stow position during at least the initial stages of the seatback frame's movement.

6. The seat frame assembly of claim 1 wherein each of the two pivot legs are connected, respectively, on either side of the forward portion of the seat base frame, and wherein the electric drive motor is connected to one of the pivot legs.

7. The seat frame assembly of claim 6 wherein at least one of the pivot legs includes a force-assist element operably connected to the pivot leg to provide a biasing force which urges the pivot leg to rotate upward from its generally horizontal stow position to its generally vertical use position.

8. The seat frame assembly of claim 1 further including at least one seatback frame force-assist element operably mounted on the seatback frame and one of the seatback/seat base interconnecting brackets to provide a biasing force on the seatback frame urging the seatback frame forward from its use position toward the stow position.

9. The seat frame assembly of claim 8 wherein at least one of the at least one seatback frame force-assist elements is a lost motion spring which provide a biasing force on the seatback frame at the initial stages of movement of the seatback frame from its use position to its stowed position.

10. A vehicle seat for a vehicle having a floor, the vehicle seat comprising:
a seat base including a seat base frame defining a top surface, the seat base frame being pivotally connected to the vehicle floor by a riser assembly, the riser assembly including at least two pivot legs, each of which pivot legs are connected at their lower end for pivotal rotation with respect to the vehicle floor, and at their upper end for pivotal rotation with respect to the seat base frame for movement between a raised use position and a lowered stow position, at least one seat base pad having a top surface and covering at least the top surface of the seat base frame, and at least one seat base trim cover covering at least the top surface of the seat base pad;
a seatback including a seatback frame defining a forward facing surface, the seatback frame being pivotally attached to the seat base frame for movement to and from a raised generally vertical use position to a lowered, generally horizontal stow position, wherein the riser assembly further includes
at least two seatback/seat base interconnecting brackets, each of the seatback/seat base interconnecting brackets are connected at their forward ends to the seat base frame, and pivotally connected at their upper ends to the seatback frame for rotation of the seatback frame about a first pivoting axis, and
at least two seatback attachment brackets, each of the seatback attachment brackets are connected at their lower ends to the vehicle floor, and pivotally connected at their upper ends to the seatback frame for rotation of the seatback frame about a second pivoting axis that is lower than the first pivoting axis from a generally vertical orientation to a generally horizontal orientation with respect to the vehicle floor, such that pivotal rotation of the lower ends of the pivot legs with respect to the vehicle floor results in a corresponding forward and downward movement of the seatback frame and the seat base frame from their use positions to their stow positions,
the seatback further including at least one seatback pad having a forward facing surface and covering at least the forward facing surface of the seatback frame, and at least one seatback trim cover covering at least the top surface of the seatback pad; and
an electric drive motor operatively connected to provide a relative torque between the seat base frame and one of the pivot legs for powered movement of the seat base frame to and from the use position and the stow position.

11. The vehicle seat of claim 10 wherein the seat base frame is connected to the vehicle floor by a riser assembly including at least two pivot legs, each of which pivot legs are connected at their lower end for pivotal rotation with respect to the vehicle floor, and at their upper end for pivotal rotation with respect to the seat base frame, and wherein the electric drive motor is operably connected to at least one of the pivot legs to drive the pivot legs from the generally vertical orientation whereby the seat base frame is in its use position, to a generally horizontal orientation whereby the seat base frame is in its stow position.

12. The vehicle seat of claim 10 wherein the drive motor is mounted in a stationary position with respect to the vehicle floor.

13. The vehicle seat assembly of claim 10 further including at least one seat base force-assist element operably connected to at least one of the pivot legs to provide a biasing force which urges the pivot legs to rotate toward the seat base use position during at least the initial stages of the seat base's movement.

14. The vehicle seat of claim 10 further including at least one seatback frame force-assist element operably mounted on the seatback frame and one of the seatback/seat base interconnecting brackets to provide a biasing force on the seatback frame urging the seatback frame forward from its use position toward the stow position during at least the initial stages of the seatback frame's movement.

15. The vehicle seat of claim 10 wherein at least one of the at least one seatback frame force-assist elements is a lost motion spring which provide a biasing force on the seatback frame at the initial stages of movement of the seatback frame from its use position to its stowed position.

16. A vehicle seat for a vehicle having a floor, the vehicle seat comprising:
a seat base including a seat base frame defining a top surface, the seat base frame being pivotally connected to the floor of the vehicle by a riser assembly, the riser assembly including at least two pivot legs, each of the pivot legs are pivotally connected at their lower ends to the vehicle floor for rotation of the pivot legs from a generally vertical orientation to a generally horizontal orientation with respect to the vehicle floor, and each of the of pivot legs are pivotally connected at their upper ends to the seat base frame, such that pivotal rotation of the lower ends of the pivot legs with respect to the vehicle floor results in a corresponding forward and downward movement of the seat base from a use position to a stow position, at least one seat base force-assist element operably connected to at least one of the pivot legs to provide a biasing force which urges the pivot legs to rotate toward the seat base use position during at least the initial stages of the seat base's movement, at least one seat base pad having a top surface and covering at least the top surface of the seat base frame, and at least one seat base trim cover covering at least the top surface of the seat base pad;
a seatback including a seatback frame defining a forward facing surface, the seatback frame being connected to the vehicle floor by the riser assembly which also includes at least two seatback/seat base interconnecting brackets, each of the seatback/seat base interconnecting brackets are connected at their forward ends to the seat base frame, and pivotally connected at their upper ends to the seatback frame for rotation of the seatback frame about a first pivoting axis, and at least two seatback attachment brackets, each of the seatback attachment brackets are connected at their lower ends to the vehicle floor, and pivotally connected at their upper ends to the seatback frame for rotation of the seatback frame about a second pivoting axis that is lower than the first pivoting axis from a generally vertical orientation to a generally horizontal orientation with respect to the vehicle floor, such that pivotal rotation of the lower ends of the pivot legs with respect to the vehicle floor results in a corresponding forward and downward movement of the seatback frame and the seat base frame from their use positions to their stow positions pivotally attached to the seat base frame for movement to and from a raised generally vertical use position to a lowered, generally horizontal stow position, at least one seatback frame force-assist element operably mounted on the seatback frame and one of the seatback/seat base interconnecting brackets to provide a biasing force on the seatback frame urging the seatback frame forward from its use position toward the stow position during at least the initial stages of the seatback frame's movement, the seatback further including at least one seatback pad having a forward facing surface and covering at least the forward facing surface of the seatback frame, and at least one seatback trim cover covering at least the top surface of the seatback pad; and an electric drive motor mounted in a stationary position with respect to the vehicle floor and operably connected to the seat base frame for powered movement of the seat base to and from the use position and the stow position, and wherein the drive motor is operably connected to provide a relative torque between the seat base frame and one of the at least two pivot legs for powered movement of the seat base to and from the use position and the stow position.

* * * * *